(12) United States Patent
Tourrel et al.

(10) Patent No.: US 9,974,945 B2
(45) Date of Patent: May 22, 2018

(54) TRANSMODIOLAR ELECTRODE ARRAY AND A MANUFACTURING METHOD

(71) Applicant: Oticon Medical A/S, Smørum (DK)

(72) Inventors: Guillaume Tourrel, Smørum (DK); Dan Gnansia, Smørum (DK); Nicolas Veau, Smørum (DK)

(73) Assignee: OTICON MEDICAL A/S, Smørum (DK)

( * ) Notice: Subject to any disclaimer, the term of this patent is extended or adjusted under 35 U.S.C. 154(b) by 0 days. days.

(21) Appl. No.: 14/934,916

(22) Filed: Nov. 6, 2015

(65) Prior Publication Data

US 2016/0129240 A1 May 12, 2016

(30) Foreign Application Priority Data

Nov. 7, 2014 (EP) .................................. 14192294
Jul. 10, 2015 (EP) .................................. 15176260

(51) Int. Cl.
  *A61N 1/05* (2006.01)
  *A61N 1/36* (2006.01)
(52) U.S. Cl.
  CPC ....... *A61N 1/0541* (2013.01); *A61N 1/36032* (2013.01)

(58) Field of Classification Search
  CPC .......................... A61N 1/0541; A61N 1/36032
  USPC .......................................................... 607/57
  See application file for complete search history.

(56) References Cited

U.S. PATENT DOCUMENTS

| | | | |
|---|---|---|---|
| 7,194,314 B1 | 3/2007 | Richter et al. | |
| 7,914,842 B1 | 3/2011 | Greenberg et al. | |
| 8,145,322 B1 | 3/2012 | Yao et al. | |
| 2006/0225274 A1* | 10/2006 | Greenberg | A61N 1/0551 29/846 |
| 2009/0143840 A1* | 6/2009 | Middlebrooks | A61N 1/36032 607/57 |
| 2012/0035615 A1 | 2/2012 | Koester et al. | |
| 2013/0023967 A1* | 1/2013 | Stafford | A61N 5/0622 607/89 |
| 2013/0204340 A1 | 8/2013 | Conn et al. | |

* cited by examiner

*Primary Examiner* — Allen Porter, Jr.
(74) *Attorney, Agent, or Firm* — Birch, Stewart, Kolasch & Birch, LLP (57) ABSTRACT

According to an embodiment, an electrode array for a transmodiolar implant is disclosed. The implant includes a substrate, a conductive metal located at a plurality of discrete portions on the substrate; and a single layer of insulation material over the conductive metal and the substrate. The single layer of insulation material includes a plurality of apertures that expose the conductive metal, the exposed conductive metal forming a plurality of electrodes, the electrode array having a Young's modulus of at least 100 GPa.

12 Claims, 5 Drawing Sheets

TRANSMODIOLAR ELECTRODE ARRAY AND A MANUFACTURING METHOD

FIELD

The present disclosure relates to a method of manufacturing an electrode array (transmodiolar electrode array) with a high number and density of electrodes for use in a transmodiolar implant-type hearing aid. The disclosure further relates to a transmodiolar implant comprising the electrode array and a method of implanting the electrode array in the cochlea. The disclosure also relates to a cochlear implant where a transmodiolar electrode array is a return electrode when used with an intracochlear stimulation electrode array.

BACKGROUND

Figure 1A:
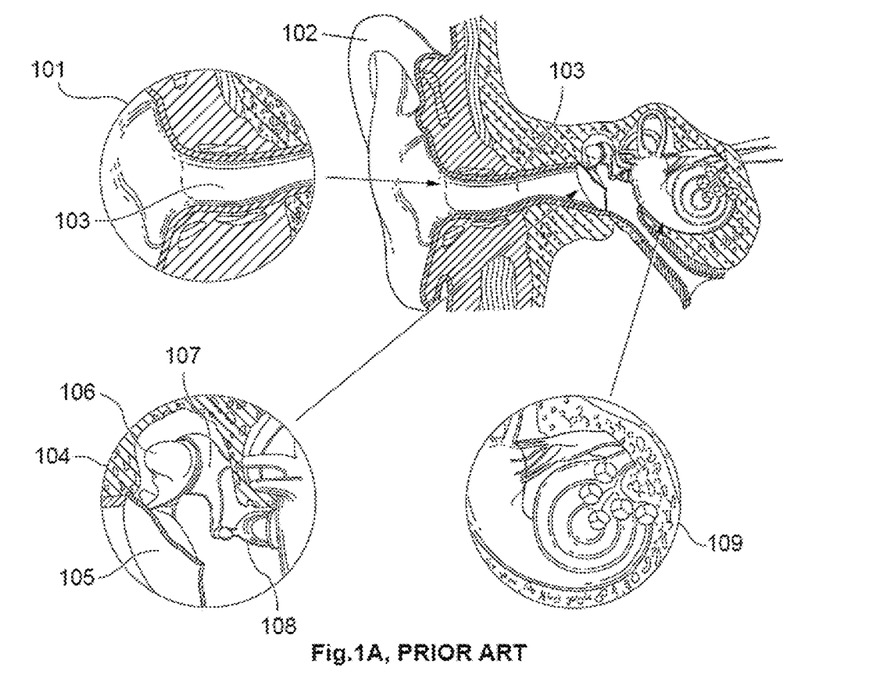
FIG. 1A illustrates the three parts of the human ear.
Figure 1B:
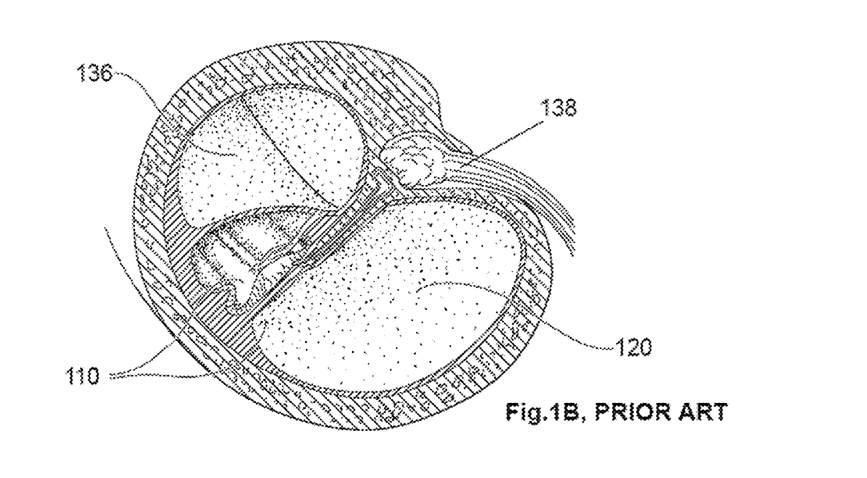
FIG. 1B illustrates a cross sectional view of the cochlea.

The human ear may be described in three parts as illustrated in FIG. 1A. The first part is the external ear 101 which includes pinna 102 for receiving and concentrating sound pressure waves to the ear canal 103. The second part is the middle ear 104 which receives the sound pressure waves from the ear canal 103. The waves pass through eardrum 105 and are transformed into mechanical vibrations that are transmitted to the ossicular chain. The vibrations pass through malleus 106, then incus 107 and finally stapes 108. The third part of the human ear is known as the inner ear or cochlea 109. A cross-section of the cochlea 109 is shown in FIG. 1B. The vibrations of the ossicular chain are transmitted from the stapes 108 to the perilymph liquid of the scala vestibuli 136 through the oval-shaped windows of the cochlea 109. Once in the cochlea 109, the vibrations in the liquid initiate the organ of Corti 110 to generate stimulus in the acoustic nerve 138.

Figure 1C:
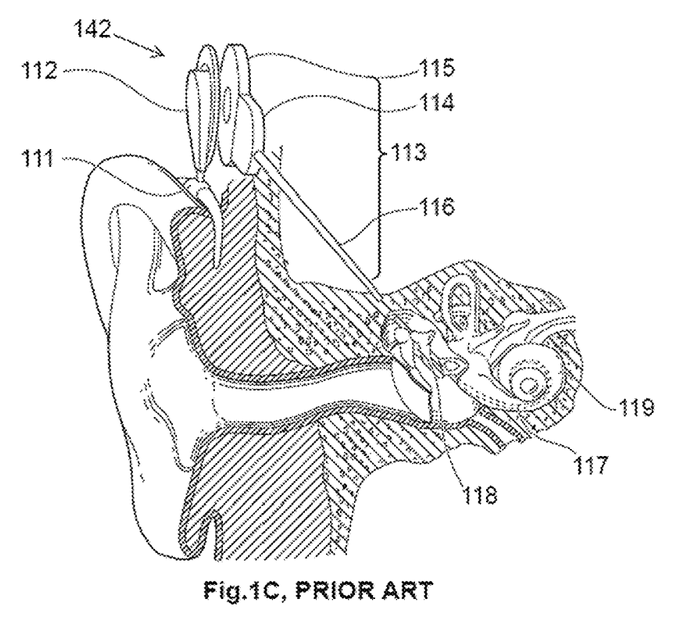
FIG. 1C illustrates a cochlear implant system according to the prior art.
Figure 1D:
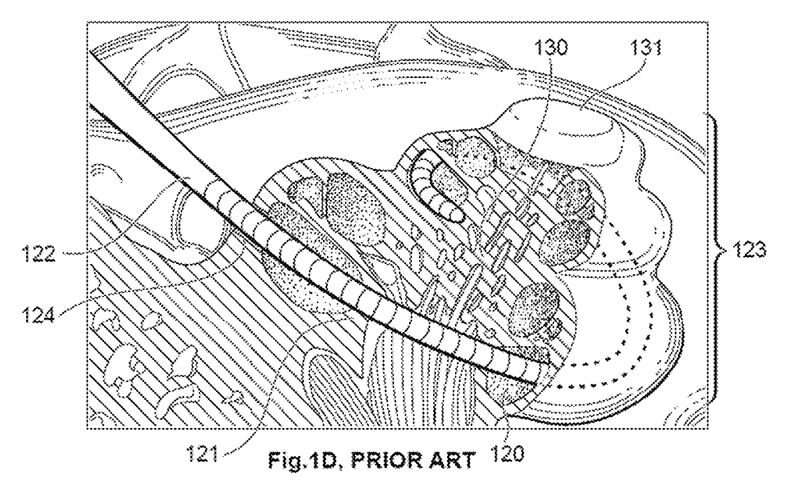
FIG. 1D illustrates a cross sectional view of an electrode array inserted into the scala tympani scala of the cochlea according to the prior art.

One type of existing hearing aid device is known as a cochlear implant. As shown in FIG. 1C, a cochlear implant 142 comprises two main parts being an external device 111 (also referred to as a speech processor) and an implantable device 113. Speech processor 111 is composed of a transmitting coil 112, a microphone, electronics, and a battery (not shown). The implantable device 113 includes a housing 114, an electronic and separate receiving coil 115, and a generally flexible lead 116 to connect the housing 114 to an electrode array 117. The flexible lead 116 passes through the middle ear 118 to reach the cochlea 119. As shown in FIG. 1D, in most instances an electrode array 121 is composed of an electrode carrier 122 made of a flexible material such as silicone in order to facilitate insertion of the array 121 into the scala tympani 120 of the cochlea 119. The scala tympani 120 has a helical shape 123 and the flexible material of carrier 122 allows for a folding effect. The electrode carrier 122 contains connection wires (not shown) that are connected to stimulation electrodes 124 made of platinum, platinum-iridium or other material having a biocompatible surface treatment.

Figures 1E, 2A:
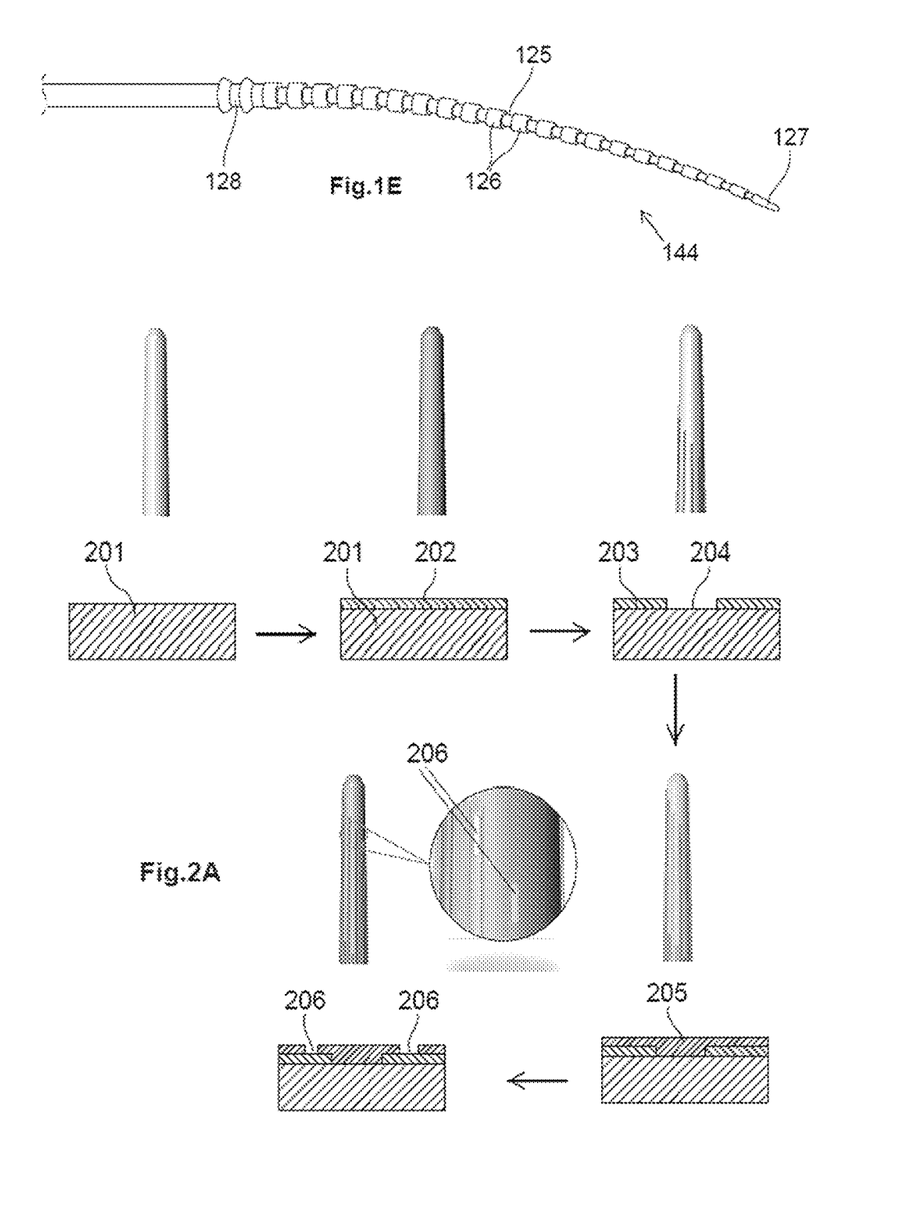
FIG. 1E illustrates a perspective view of an electrode array according to the prior art.
FIG. 2A illustrates a method of manufacturing the electrode array according to an embodiment of the disclosure.

FIG. 1E illustrates an example of an electrode array 144 composed of cylindrical electrodes 125 made of platinum-iridium. Each electrode 125 is separated from each other by a small silicone ring 126. The diameter of each silicone ring 126 regularly decreases towards proximal end 127 in order to form a progressively finer or tapered surface. Additional rings 128 are disposed on the basal diameter of the electrode array 144 to assist insertion of the array 144 into the cochlea. Generally, the electrode array of existing cochlear implants has an average of one electrode per each one millimeter along the array.

A problem with existing cochlear implant systems is the realization of spatially high-resolution electrical stimulation to restore sound perception close to normal hearing. The stimulating current usually diffuses and stimulates a large number of spiral ganglia with low specificity if the electrode array is located far from the target cells. It is thus important to locate the electrode array close to the spiral ganglia in the cochlea (the target of the electrical stimulation). As described above and in FIG. 1D, the electrode array of a cochlear implant is generally inserted into the scala tympani because it has the largest cross-sectional area and is an easy surgical operation site. Stimulating currents flowing from the electrode site stimulate the spiral ganglion cells located in the direction of the cochlea modiolus. Therefore, it is desirable to locate the electrode array of a cochlear implant system close to the modiolus to reduce the distance between the electrode and the spiral ganglia and increase the spatial specificity of the electrical stimulation.

Several strategies have been developed and employed in cochlear implant systems to locate the electrode close to the modiolus. For example, modiolus-hugging electrodes are developed, these electrode use a carrier which is held straight by an internal stylet before and during the insertion process in the scala tympani. After the partial insertion of the electrode and stylet, the electrode is pushed to its full insertion depth while holding the stylet at the same position. The electrode returns to its original spiral shape while being pushed toward the modiolus. Accordingly, the insertion depth of the stylet is critical in modiolus-hugging electrode array surgery. If the stylet is inserted far deeper into the cochleostomy, the electrode tip will come into contact with the cochlear outer wall, which may damage the spiral ligament or penetrate into the scala vestibuli. On the other hand, if the insertion depth of the stylet is too short, the apical curve of the electrode will curl before the first turn of the scala tympani. Thus, previous efforts to facilitate current flow through the modiolus included fabrication and use of precurved electrodes designed to "hug" the modiolus and silastic positioners designed to place the electrodes closer to the modiolus.

Another aspect about electrical stimulation of the auditory system includes completion of a circuit loop whereby one electrode along the intracochlear electrode array serves as the active electrode and a second serves as a return electrode. Monopolar stimulation mode is the most commonly used strategy where the second extracochlear return electrode is located on the case of the receiver-stimulator unit. Bipolar stimulation mode, on the other hand, uses a neighboring electrode within the implanted intracochlear electrode array as the return. Various variations such as bipolar+1 or bipolar+2 are also possible. Other modes may include tripolar stimulation mode where current is delivered to one intracochlear electrode and its two neighboring electrodes serve as return electrodes. With different stimulation modes, one can achieve some advantages or face challenges such as in the area of power consumption and specificity of stimulation.

None of the currently available solution overcomes the above-mentioned shortcomings. Therefore, there is a need to provide a solution that allows for an extremely high number of contact electrodes in an array and/or to provide an alternative to current stimulation modes.

SUMMARY

The disclosure relates to transmodiolar electrode array that is suitable for transmodiolar implantation. The electrode array is placed into the modiolus rather than into the scala tympani, which is a conventional location for a cochlear implant electrode array. The modiolus is a conical shaped central axis in the cochlea. It consists of spongy bone and the cochlea turns around it. The spiral ganglion is situated inside the modiolus. The principle according to an embodiment is to stimulate directly the inner auditory nerve at the departure of the cochlea. In order to achieve this, a transmodiolar electrode is required, the transmodiolar electrode being placed into the modiolus.

Utilizing the transmodiolar electrode and its placement in the modiolus allows for realizing spatially high-resolution electrical stimulation, i.e. reducing distance between the electrode and the spiral ganglia and increasing the spatial specificity of the electrical stimulation. The diffusion of stimulating current into the perilymph liquid, as encountered with electrode arrays of conventionally implanted cochlear implant systems, is countered. Furthermore, utilizing the transmodiolar electrode adapted to directly stimulate the inner auditory nerve allows for reducing the physical distance between the current source and the target, thus reducing the current necessary to stimulate nerve fibers. Also, lower currents minimize interactions between neighboring stimulating electrodes, and lessen the risk of damage due to current application. Thus, in an embodiment, the transmodiolar electrode array is adapted to be positioned within a modiolus of a user, to receive electrical pulses from the stimulator and using the electrodes, to directly stimulate auditory nerve fibre of the user.

The implantation may be achieved by a procedure that involves an external ear canal-type approach. According to an illustrative embodiment, a method of implanting an electrode array in the cochlea of a subject is disclosed. The method includes providing a transmodiolar electrode array or a transmodiolar implant including the transmodiolar array, drilling through a bony sulcus of the cochlea to access the modiolus, and inserting the electrode array into the modiolus.

The above method may be achieved by prior to the drilling, at least partially removing the tympanic membrane in order to access the middle ear, giving access to the bony sulcus near malleus and stapes. Thereafter, creating a pathway into the modiolus by the drilling through the bony sulcus into the apex. After the placement of the lead including the transmodiolar electrode along the drilled canal pathway for accessing the modiolus, the canal is covered with bone powder and cement.

The stimulator may be latched onto the temporal bone as in existing cochlear implantations.

In an embodiment, the transmodiolar electrode array is less than approximately 8 mm such as less than 7 mm such as less than 6 mm and has a width/diameter of less than approximately 0.6 mm, such as 0.5 mm, or 0.4 mm. As an example, for a 6 mm length of transmodiolar electrode array, about 1 mm passes through the bone of the cochlea and the remaining length of about 5 mm is the active area containing the electrode array. It will be apparent to the skilled person that variations in the stated dimensions are possible. Therefore, such variations are within scope of this disclosure.

The electrode arrays used in traditional cochlear implant systems are unsuitable for transmodiolar implantation due to the type, shape, and/or geometry of the electrode array in the cochlear implant system. For example, the electrode arrays conventionally used for cochlear implant with an insertion into the cochlea are flexible enough to allow for folding effect, a property that is generally not desirable for transmodioloar electrode. In fact, one of the criteria for conventional intracochlear electrode array is to have stiffness that is low enough to facilitate folding and this requirement may become even more critical for atraumatic electrode array. Typically silicone is used as a carrier in such introcochlear electrode arrays, having Young's modulus around 0.01 GPa. Furthermore, conventional electrode array in a cochlear implant lacks a sufficient number of electrodes in a small length available for transmodiolar implantation because each conventional electrode is made of a relatively large platinum core that cannot be manufactured in a smaller size with existing methods.

An embodiment disclosed herein relates to a method of manufacturing an electrode array for a transmodiolar implant. The method includes providing a substrate and applying a conductive metal to a plurality of discrete portions on the substrate. A layer of insulation material is then applied over the conductive metal and the substrate. Finally, a plurality of portions of the insulation material is selectively removed in order to expose the conductive metal thereby forming a plurality of electrodes. The electrode array comprises a Young's modulus of at least 100 GPa.

In an embodiment, the applied layer of insulation material includes a single layer from which the plurality of portions are selectively removed.

In some embodiments, the step of applying a conductive metal to a plurality of discrete portions on the substrate includes applying a layer of conductive metal to the substrate; followed by selectively removing a plurality of portions of the conductive metal from the applied layer to expose the substrate.

According to an embodiment, the plurality of portions of the conductive metal are selectively removed by laser ablation.

In an alternative embodiment, the step of applying a conductive metal to a plurality of discrete portions on the substrate includes applying a cover having a plurality of apertures to the substrate; applying a conductive metal to the cover; and removing the cover to expose the conductive metal and the substrate.

Utilizing a cover allows the person skilled in the art to avoid having to selectively remove a plurality of portions of the conductive metal from the applied layer for example, by laser ablation as described immediately above.

In an embodiment, the cover comprises a UV curing resin.

In some embodiments, the substrate is not electrically conductive, i.e. electrically non-conductive.

According to some embodiments, the substrate is selected from the group consisting of alumina, zirconia, zirconia alumina composite, PEEK (polyether ether ketone), PI, and PMMA (Poly(methyl methacrylate)). The alumina may be a high purity alumina. Other long term implantable plastics may also be utilized as the substrate.

In some embodiments, the conductive metal is selected from the group consisting of titanium, gold, platinum, iridium and mixtures thereof. The conductive metal may be an alloy of two or more metals.

In some embodiments, the conductive metal is applied by serigraphy.

In alternative embodiments, the conductive metal is applied by deeping of a conductive paint prior to heating in a furnace.

In some embodiments, the conductive paint is a titanium hydrate solution.

In alternative methods, the conductive metal is applied by sputtering. This allows for very good control of the thickness of the conductive metal on the substrate.

According to some embodiments, the plurality of portions of the insulation material are selectively removed by laser ablation.

According to an embodiment, an electrode array for a transmodiolar implant is disclosed. The electrode array includes a substrate, a conductive metal located at a plurality of discrete portions on the substrate; and a single layer of insulation material over the conductive metal and the substrate. The single layer of the insulation material includes a plurality of apertures that expose the conductive metal. The exposed conductive metal forms a plurality of electrodes.

In some embodiments, the electrode array of the aspects described above further includes a reference electrode located at one end of the electrode array; and a connection member in contact with the reference electrode for connecting the electrode array to a lead from a cochlear stimulator.

In some embodiments, the electrode array further comprises connection wires in the connection member.

In some embodiments, the electrode array is stiff. This facilitates insertion into the modiolus of a subject/CI user. The electrode array may be substantially straight when inserted. As opposed to intracochlear electrode array, the stiffness and/or straightness is critical because the transmodiolar array needs to be adapted to be inserted in the modiolus. The stiffness of the transmodiolar electrode array, expressed in Young's modulus, is significantly higher than the Young's Modulus of silicon, which is used for producing intracochlear electrode array. For example, the Young's modulus of the transmodiolar electrode array is at least 350 times than that of the silicon such as 500 times, or 750 times or 1000 times. Preferably, the Young's modulus for the transmodiolar electrode array is typically at least 100 GPa, such as at least 125 GPa, such as at least 150 GPa such as at least 175 GPa or at least 200 GPa. An example of such electrode array would include zirconia substrate based transmodiolar electrode array having Young's modulus of 210 GPa. In an embodiment, the stiffness of the transmodiolar electrode array varies along the length of the electrode array such that the stiffness at the distal end section is lower than that that at the other end.

In one embodiment, at least two electrodes of the electrode array are of substantially same size and shape. Additionally or alternatively, at least two electrodes of the electrode array are substantially different in size and shape.

In another embodiment, at least two electrodes of the electrode array are spaced evenly apart from each other. Additionally or alternatively, at least two electrodes of the electrode array are spaced unevenly apart from each other.

In one embodiment, the electrodes are spaced apart along length of the electrode array. In an embodiment, the electrodes are spaced apart along width or circumference of the electrode array.

In a particular embodiment, the electrodes are spaced apart along length of the transmodiolar electrode array such that a pair of neighboring electrodes are at different distances from a distal end of the electrode array and spaced apart around circumference of the transmodiolar electrode array. The distal end is defined as the tip of the electrode array. In comparison to same length conventional intracochlear electrode array having spaced apart electrodes only along its length, the transmodiolar electrode array comprising circumferentially spaced apart electrodes allows for creating enough spacing between neighboring electrodes, thereby controlling channel interaction. Also, combining the spaced apart electrodes along the length and circumference of the transmodiolar electrode array allows for accommodating more electrodes for a predefined length of the electrode array in comparison to conventional intracochlear electrode array.

In an embodiment, the electrodes are spaced apart along length of the transmodiolar electrode array and spaced apart around circumference of the transmodiolar electrode array such that the electrodes form a specific pattern such as at least one helical pattern around the circumference of the transmodiolar electrode array. This allows for having a pattern that is adapted to directly face auditory nerve fibre. Alternatively, the pattern may include a circular pattern.

In one embodiment, the electrodes include exposed metal tracks along length of the array.

It would be apparent to the skilled person that a combination of the above variations is possible in order to provide a design that allows for higher specificity of the electrical signals and/or arrangement of the electrode within the modiolus.

In some embodiments, the electrode array is formed on a flat surface, convex surface, or concave surface of the substrate.

In an embodiment, the substrate is cylindrical.

According to yet another aspect, a transmodiolar implant is disclosed. The implant includes a transmodiolar electrode array, a cochlear stimulator and a flexible lead. The electrode array includes an array that is described by any or by combining aspects or embodiments described above. The cochlear stimulator is configured to provide electrical signals to the electrode array when position within the modiolus. The flexible lead connects the electrode array to the cochlear stimulator.

In another aspect disclosed herein is a method of implanting an electrode array in the cochlea of a subject. The method includes providing an electrode array or a transmodiolar implant according to any one of or combining the aspects or embodiments described above. Thereafter, drilling through the bony sulcus of the cochlea to access the modiolus; finally and inserting the electrode array into the modiolus.

According to some embodiments, the number of electrodes in the electrode array may vary. For example, the number may include at least 16 electrodes, such as at least 18 electrodes and preferably at least 20 electrodes such as 22 electrodes or more.

Another aspect disclosed herein relates to an electrode array for a transmodiolar implant manufactured by the method according to any one of the aspects or embodiments described above.

In one embodiment, instead of using the transmodiolar electrode array for stimulating the auditory nerve fiber as disclosed earlier, the transmodiolar electrode array is used as a return/reference electrode in combination with an intracochlear electrode array that is adapted to be positioned within the cochlea. In this embodiment, electrodes of the intracochlear electrode array are adapted to produce the stimulation that produces auditory percept. The electrical circuit comprises i) a signal generator of the stimulator providing the electrical stimulation pulse, ii) an active electrode of the intracochlear stimulation electrode array, and iii) transmodiolar electrode array as a return electrode. The active electrode of the intracochlear electrode is typically located in scala tympani whereas the transmodiolar return electrode is positioned within the cochlea modiolus of the subject/user. The proximity of the transmodiolar return electrode to the cochlear electrode array allows for better stimulation because of shorter current path between the cochlear electrode array and transmodiolar return electrode when compared for example to conventional monopolar stimulation mode. In particular, modiolar current (responsible for neural excitation) amplitudes is influenced significantly by location of the return electrode, being larger when placed into the modiolus. Placing a cochlear implant's return electrode in the modiolus significantly reduce its power consumption. Reducing power requirements thus leads to improved efficiency, safer long-term use, and longer device life.

Thus, according to an embodiment, a method of positioning a cochlear implant in a user is disclosed. The method includes implanting a receiver-stimulator within a user adjacent the ear of a user, positioning an intracochlear electrode array within a cochlea of the user, and positioning the transmodiolar electrode array within the modiolus of the user, the transmodiolar electrode array being adapted to be used as a return electrode.

Positioning of the receiver-stimulator and intracochlear electrode array within the cochlea is performed in accordance with the known techniques. The transmodiolar electrode array is adapted to be used as a return electrode. In different embodiment where the transmodiolar electrode array is used as a return electrode, the transmodiolar electrode array may include either transmodiolar electrode features that are described in this disclosure or a single electrode positioned within the modiolus. For same sized return electrode, the latter is preferred as it provides a larger return electrode surface area. Positioning of the transmodiolar return electrode may be achieved by drilling through a bony sulcus of the cochlea to access the modiolus; and inserting the transmodiolar electrode array into the modiolus.

In accordance to another embodiment, an implanted part of a cochlear implant is disclosed. The implanted part includes a receiver-stimulator, an intracochlear electrode array and a transmodiolar electrode array. The receiver-stimulator includes a tuned coil and a signal generator. The tuned coil is adapted to receive data information and power using an inductive link from a patient-wearable speech processor. The signal generator is adapted to generate channel specific electrical pulse in accordance with the received data information. Each electrode of the intracochlear electrode array defines a specific frequency channel and are frequency-place mapped within the cochlea. In an example, the intracochlear electrode array may typically be composed of conductive, corrosion-resistant, noble metal platinum-irridium alloy electrodes separated by flexible poly(dimethyl siloxane) (silicone rubber) insulation. The electrodes of the intracochlear electrode array is adapted to deliver the channel specific electric pulse generated by the signal generator. The transmodiolar electrode array is used as a return electrode and comprises one or more features that are described in this disclosure or a single electrode.

BRIEF DESCRIPTION OF DRAWINGS

The aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other aspects. These and other aspects, features and/or technical effect will be apparent from and elucidated with reference to the illustrations described hereinafter in which:

DETAILED DESCRIPTION

The detailed description set forth below in connection with the appended drawings is intended as a description of various configurations. The detailed description includes specific details for the purpose of providing a thorough understanding of various concepts. However, it will be apparent to those skilled in the art that these concepts may be practiced without these specific details.

FIG. 2A illustrates a method of manufacturing an electrode array according to an embodiment of the disclosure. In the method a layer of conductive metal 202 is deposited onto a substrate 201 by for example, serigraphy. A portion of the conductive metal is then selectively removed from the layer of conductive metal 202 such as by an ablation technique to expose the substrate 201 and create conductive areas 203 separated by an insulation zone 204. The conductive area 203 acts as an electrical track or electrode.

In an alternative embodiment (not illustrated), a mask or cover having a plurality of apertures or slits or tracks is first applied to the substrate. A conductive metal is applied to the cover by for example, sputtering, and the cover is removed to expose the conductive areas 203 and the insulation zone 204. This alternative embodiment allows for avoiding use of the ablation technique to selectively remove a portion of conductive metal from the layer of conductive metal 202.

Although FIG. 2A illustrates two conductive areas 203 and one insulation zone 204, it will be understood that the method creates many conductive areas 203 and insulation zones 204 on the substrate 201. Deposition of a thin insulation layer 205 then completely covers the substrate 201, conductive areas 203, and insulation zone(s) 204. A plurality of portions of the insulation material 205 are then selectively removed by laser ablation to form windows 206 which expose the conductive areas 203 containing the conductive metal thereby forming the electrode array.

In an example, a substrate made of high resistance zirconia is used as a substrate 201 and electrical tracks and surface electrodes 202 were realized by metallization of gold and platinum. Thereafter, laser ablation is performed is performed and a layer of insulation material 205 such as parylen coating is applied. Surface electrodes 206 are revealed by locally removing the insulation material 205 using laser ablation.

Figure 2B:
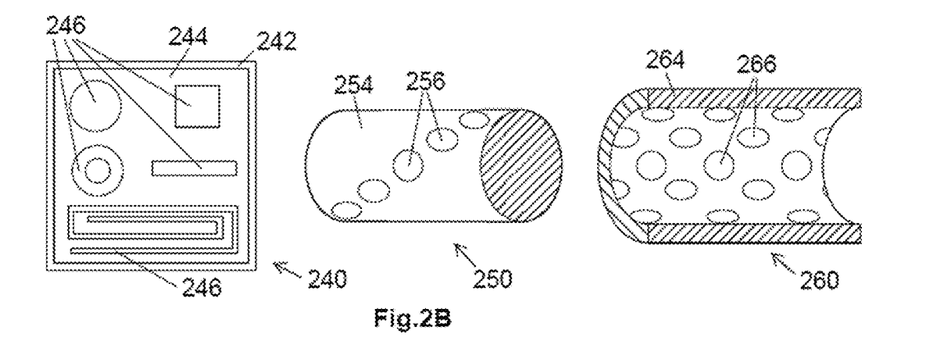
FIG. 2B illustrates different patterns of electrode arrays that may be manufactured according to an embodiment of the disclosure.

FIG. 2B illustrates different patterns of electrode arrays that may be manufactured according to an embodiment of the disclosure. Electrode array 240 has a flat surface with several different sizes and shapes of surface contact electrodes 246. The substrate 242 and insulation layer 244 are also shown in electrode array 240. The flat surface may take any suitable shape such as a square, rectangle or oval. Electrode array 250 is formed on a substrate having a cylindrical shape with an insulation layer 254 and multiple electrodes 256 of substantially uniform size and shape that are spaced evenly apart from each other. In electrode array 260 the electrodes 266 are formed on a substrate with a concave surface. Insulation layer 264 is also illustrated in electrode array 260. Other shapes and surfaces (not illustrated) may also be used for example, a conical shape or a convex surface. The different electrode patterns in FIG. 2B show that the method of manufacturing an electrode array may be tailored as desired in order to obtain multiple contact areas and any number of desired styles or shapes of electrical tracks/electrodes.

In a particular embodiment, the electrodes are spaced apart along length of the transmodiolar electrode array such that a pair of neighboring electrodes are at different distances from a distal end of the electrode array and spaced apart around circumference of the transmodiolar electrode array. The distal end (see 252, FIG. 2D) is defined as the tip of the electrode array. This is illustrated FIG. 2B, in a first implementation electrodes 256 and in a second implementation electrode 266 and also in FIG. 2A as 206.

In an embodiment, the electrodes are spaced apart along length of the transmodiolar electrode array and spaced apart around circumference of the transmodiolar electrode array such that the electrodes form a specific pattern such as at least one helical pattern (FIG. 2B, 256, 266) around the circumference of the transmodiolar electrode array.

Figure 2C:
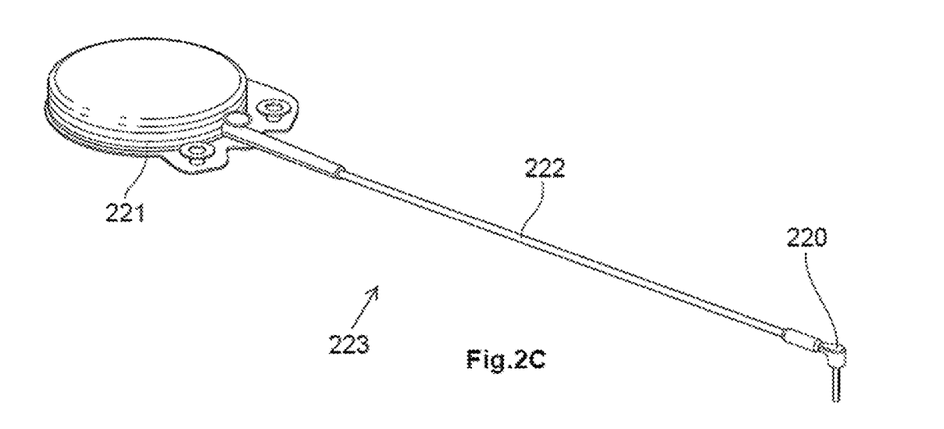
FIG. 2C illustrates a perspective view of a transmodiolar implant having an electrode array suitable for transmodiolar implantation according to an embodiment of the disclosure.

FIG. 2C illustrates a transmodiolar implant 223 composed of an electrode array 220 connected to a cochlear stimulator 221 through a flexible lead 222. The electrode array 220 is coated with silicone to ensure a smooth surface. Electrode array 220 may be manufactured by the method according to the present disclosure as described above.

Figure 2D:
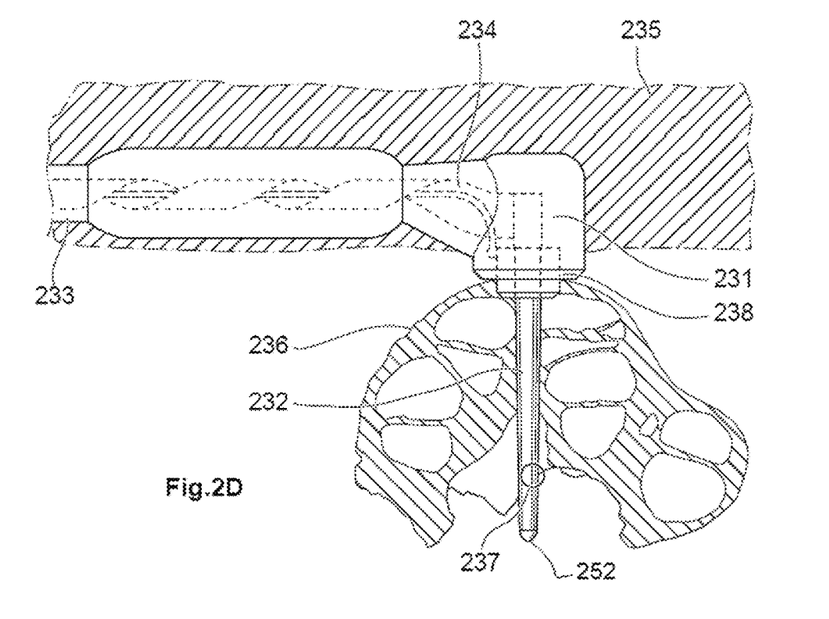
FIG. 2D illustrates a detailed view of an electrode array implanted in the cochlea of a subject according to an embodiment of the disclosure.

FIG. 2D illustrates an electrode array implanted in the cochlea of a subject. The connection member 231 is located at the transition between the middle ear 235 and the cochlea 236. Connection member 231 functions to connect the active area 232 of the electrode array with lead 233 from the stimulator (not shown) using connection wires 234 located in the connection member 231. The connection member 231 must be able to resist handling by a surgeon using a micro forceps or other specific surgical tool as well as withstand bone growth subsequent to implantation. The active area 232 of the electrode array is inserted into the modiolus of the cochlea after opening by the surgeon. Active area 232 is composed of a high number of stimulating electrodes and/or recording electrodes 237. For example, at least twenty active electrodes are present in area 232. The active electrodes are made of a stable, biocompatible platinum-iridium material that is used in implantable medical devices. Non-limiting examples of suitable electrodes 237 in active area 232 are electrodes forming part of the electrode arrays 240, 250, or 260 as described above and as illustrated in FIG. 2B. The active area 232 also includes a reference electrode 238 in the shape of a ring placed at one end of the active area 232.

It is intended that the structural features of the devices described above, either in the detailed description and/or in the claims, may be combined with steps of the method, when appropriately substituted by a corresponding process.

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element but an intervening elements may also be present, unless expressly stated otherwise. As used herein, the term "and/or" includes any and all combinations of one or more of the associated listed items. The steps of any disclosed method is not limited to the exact order stated herein, unless expressly stated otherwise.

It should be appreciated that reference throughout this specification to "one embodiment" or "some embodiments" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

The claims are not intended to be limited to the aspects shown herein, but is to be accorded the full scope consistent with the language of the claims, wherein reference to an element in the singular is not intended to mean "one and only one" unless specifically so stated, but rather "one or more." Unless specifically stated otherwise, the term "some" refers to one or more.

Accordingly, the scope should be judged in terms of the claims that follow.

The invention claimed is:

1. A electrode array comprising:
   a substrate having a cylindrical shape;
   a conductive metal located at a plurality of discrete portions on the substrate; and
   a single layer of insulation material over the conductive metal and the substrate;
   wherein the single layer of insulation material comprises a plurality of apertures that expose the conductive metal, the exposed conductive metal forming a plurality of electrodes that are spaced apart around the circumference of the cylindrical shaped substrate such that the electrodes form at least one circular or helical pattern around the circumference of the cylindrical shaped substrate while the cylindrical shaped substrate is in a substantially straight orientation, and
   wherein the substrate and the conductive metal of the electrode array each have a Young's modulus of at least 100 GPa.

2. The electrode array according to claim 1, further comprising
   a reference electrode located at one end of the electrode array; and
   a connection member in contact with the reference electrode for connecting the electrode array to a lead from a cochlear stimulator.

3. The electrode array according to claim 2, further comprising connection wires in the connection member.

4. The electrode array according to claim 3, wherein the electrodes are spaced apart along a length of the cylindrical shaped substrate such that a pair of neighboring electrodes are at different distances from a distal end of the cylindrical shaped substrate and spaced apart around the circumference of the cylindrical shaped substrate.

5. The electrodes array according to claim 3, wherein the electrodes are spaced apart along length of the cylindrical shaped substrate and spaced apart around the circumference of the cylindrical shaped substrate such that the electrodes form at least one helical pattern around the circumference of the cylindrical shaped substrate.

6. The electrode array according to claim 2, further comprising connection wires in the connection member.

7. The electrode array according to claim 2, wherein the electrodes are spaced apart along a length of the cylindrical shaped substrate such that a pair of neighboring electrodes are at different distances from a distal end of the cylindrical shaped substrate and spaced apart around the circumference of the cylindrical shaped substrate.

8. The electrodes array according to claim 2, wherein the electrodes are spaced apart along length of the cylindrical shaped substrate and spaced apart around the circumference of the cylindrical shaped substrate such that the electrodes form at least one helical pattern around the circumference of the cylindrical shaped substrate.

9. The electrode array according to claim 1, wherein the electrodes are spaced apart along a length of the cylindrical shaped substrate such that a pair of neighboring electrodes are at different distances from a distal end of the cylindrical substrate and spaced apart around the circumference of the cylindrical shaped substrate.

10. The electrodes array according to claim 1, wherein the electrodes are spaced apart along length of the cylindrical shaped substrate and spaced apart around the circumference of the cylindrical shaped substrate such that the electrodes form at least one helical pattern around the circumference of the cylindrical shaped substrate.

11. The electrode array according to claim 1, wherein the electrode array has a length such that when positioned within a modiolus of a user electrical pulses from a stimulator directly stimulate, using the electrodes, auditory nerve fibre of the user.

12. A transmodiolar implant comprising:
- an electrode array according to claim 1, the electrode array being configured to be placed into the modiolus;
- a cochlear stimulator configured to provide electrical signals to the electrode array when positioned within the modiolus; and
- a flexible lead connecting the electrode array to the cochlear stimulator.

* * * * *